(12) United States Patent
Bowman

(10) Patent No.: US 9,591,816 B2
(45) Date of Patent: Mar. 14, 2017

(54) ONION VARIETY DULCIANA

(71) Applicant: Nunhems B.V., Nunhem (NL)

(72) Inventor: Michael Bowman, Bakersfield, CA (US)

(73) Assignee: Nunhems B.V., Nunhem (NL)

( * ) Notice: Subject to any disclaimer, the term of this patent is extended or adjusted under 35 U.S.C. 154(b) by 783 days.

(21) Appl. No.: 14/013,302

(22) Filed: Aug. 29, 2013

(65) Prior Publication Data

US 2014/0007274 A1    Jan. 2, 2014

(51) Int. Cl.
*A01H 5/06* (2006.01)
*A01H 1/02* (2006.01)

(52) U.S. Cl.
CPC .............. *A01H 5/06* (2013.01); *A01H 1/02* (2013.01)

(58) Field of Classification Search
None
See application file for complete search history.

(56) References Cited

PUBLICATIONS

Boyhan et al. (Onion Variety Trial Results, University of Georgia Publication, made publicly available online in 2007, pp. 125-142).*

* cited by examiner

*Primary Examiner* — Brent Page
*Assistant Examiner* — Jared Shapiro

(57) ABSTRACT

The invention relates to the field of *Allium* in particular to a new variety of *Allium cepa* L. designated DULCIANA plants, seeds and bulbs thereof as well as plant breeding methods involving DULCIANA.

19 Claims, 1 Drawing Sheet

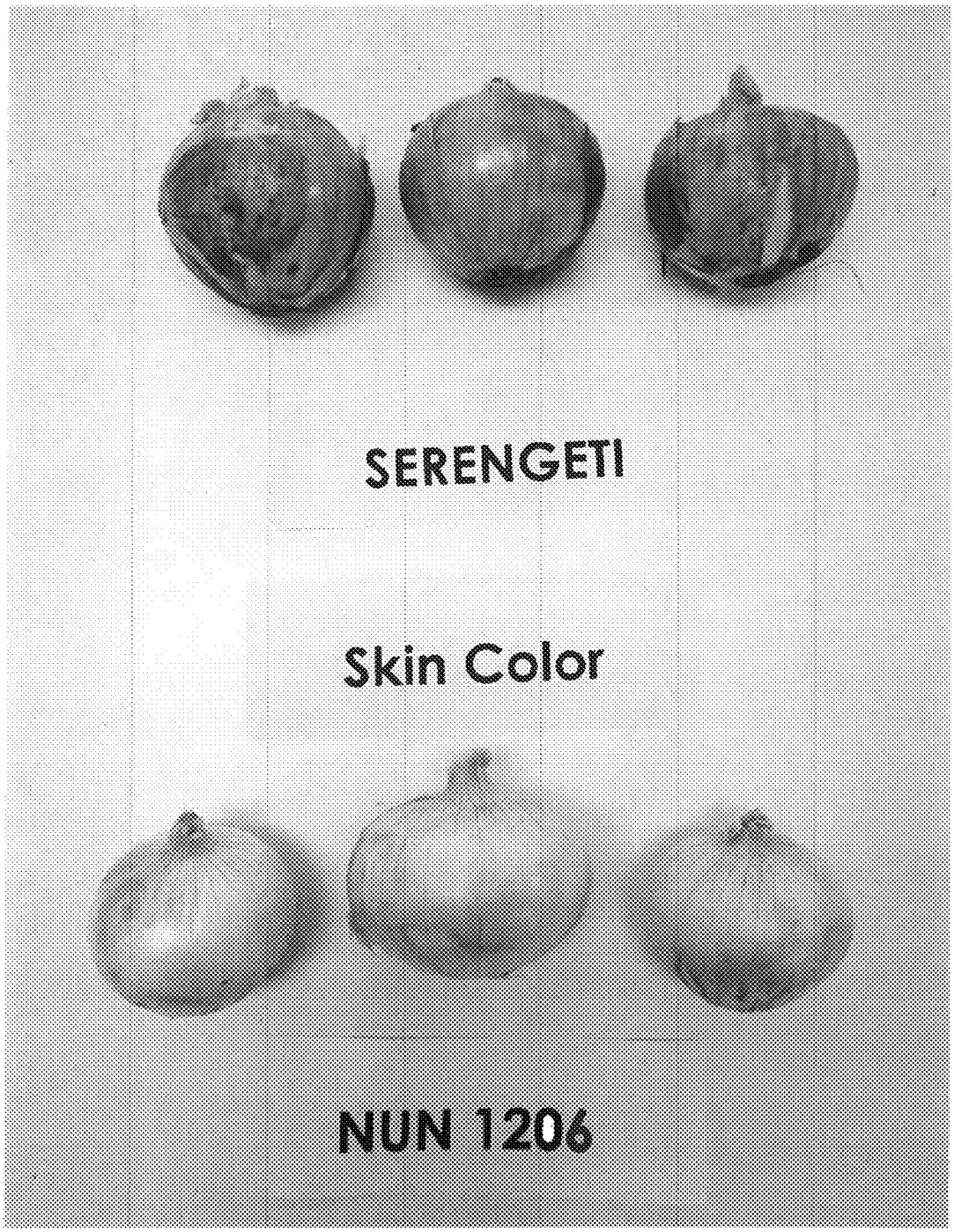

ONION VARIETY DULCIANA

FIELD OF THE INVENTION

The present invention relates to the field of plant breeding and, more specifically, to the development of onion variety DULCIANA (or NUN 01206 ON or NUN 1206.

BACKGROUND OF THE INVENTION

Onions belong to the lily family, *Amaryllidaceae*, and the genus, *Allium*. *Alliums* comprise a group of perennial herbs having bulbous, onion-scented underground leaves, including such commonly cultivated crops as garlic, chives, and shallots. It also includes ornamental species grown for their flowers.

Onions are an important vegetable world-wide, ranking second among all vegetables in economic importance with an estimated value of $6 billion dollars annually. The onion is also one of the oldest cultivated vegetables in history. The common garden onions are in the species *Allium cepa*. Onions are classified in numerous ways, by basic use, flavor, color, shape of the bulb, and day length. Onions come in white, yellow, and red colors. The bulb may be rounded, flattened, or torpedo shaped.

Commercial onions include "storage onions", "fresh onions", "pearl or mini onions", and "green onions". "Fresh onions" tend to have a lighter color with a thin skin, a milder, sweeter flavor, and must be eaten fresh as they do not store well. These onions are available in red, yellow, and white colors.

Storage onions are available from harvest, which is at the beginning of August, and are stored and available throughout the winter months up to about March. Storage onions have a darker skin that is thicker than that of a fresh onion. They are also known for intense, pungent flavor, higher percentage of solids and desirable cooking characteristics. These onions are also available in red, yellow and white colors. Not all long day length type (long day type) onions are suitable for storage. A true storage onion is one that can be harvested in late summer or fall, and stored, under proper conditions, until the spring, when the fresh onion crop is again available.

"Spanish onion", "Spanish onions", or "Spanish type" are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Onion varieties initiate bulbing when both the temperature and a minimum number of daylight hours reach certain levels. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are therefore classified by the degree of day length that will initiate bulb formation. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude, and at higher latitudes long-day onions will produce sufficient top growth before the day length triggers bulbing to produce a large bulb. A short-day onion grown in the North (higher latitudes) will bulb too early and produce relatively small bulbs.

Short day onions are preferred for southern areas such as southern Texas, southern California and Mexico. If a long day type onion is planted in such a short day climate, it may never experience enough day length to trigger the bulbing process.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugars glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties (with the exception of U.S. patent application Ser. No. 12/861,740 which is based on U.S. patent application Ser. No. 12/020,360). Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

The use of a type of onion is depending on a customer's preference for taste, aroma, appearance and color of an onion. There is thus a need for new short day onions with new appearance and color properties.

SUMMARY OF THE INVENTION

In one aspect, the present invention provides an onion plant of the variety designated DULCIANA. Parts of the onion plant of the present invention are also provided, for example, including a leaf, pollen, an ovule, a bulb and a cell of the plant.

The invention also concerns seed of onion variety DULCIANA. The onion seed of the invention may be provided as an essentially homogeneous population of onion seed. Therefore, seed of the invention may be defined as forming at least about 97% of the total seed, including at least about 98%, 99% or more of the seed. The population of onion seed may be particularly defined as being essentially free from non-hybrid seed. The seed population may be separately grown to provide an essentially homogeneous population of onion plants according to the invention. Also encompassed are plants grown from seeds of onion variety DULCIANA and plant parts thereof such as a leaf, pollen, an ovule, a bulb and a cell.

Another aspect refers to an onion plant, or a part thereof, having all or essentially all the physiological and morphological characteristics of an onion plant of onion variety DULCIANA.

In another aspect of the invention, a tissue culture of regenerable cells of a plant of variety DULCIANA is provided. The tissue culture will preferably be capable of regenerating plants capable of expressing all of the physiological and morphological characteristics of a plant of the invention, and of regenerating plants having substantially the same genotype as other such plants. Examples of some such physiological and morphological characteristics include those traits set forth in Table 1 herein. The regenerable cells in such tissue cultures may be derived, for example, from embryos, meristems, cotyledons, pollen, leaves, anthers, roots, root tips, pistil, flower, seed and stalk. Thus, a tissue culture may comprise regenerable cells from embryos, meristems, cotyledons, pollen, leaves, anthers, roots, root tips, pistil, flower, seed and bulbs. Still further, the present invention provides onion plants regenerated from a tissue culture of the invention, the plants having all the physiological and morphological characteristics of a plant of the invention.

The invention also concerns methods of vegetatively propagating a plant of the invention. In certain embodiments, the method comprises the steps of: (a) collecting tissue capable of being propagated from a plant of the invention; (b) cultivating said tissue to obtain proliferated shoots; and (c) rooting said proliferated shoots to obtain rooted plantlets. In some of these embodiments, the method further comprises growing plants from said rooted plantlets.

In yet another aspect of the invention, processes are provided for producing onion seeds, plants and bulb, which processes generally comprise crossing a first parent onion plant with a second parent onion plant, wherein at least one of the first or second parent onion plants is a plant of the variety designated DULCIANA.

These processes may be further exemplified as processes for preparing hybrid onion seed or plants, wherein a first onion plant is crossed with a second onion plant of a different, distinct variety to provide a hybrid that has, as one of its parents, the onion plant variety DULCIANA.

In another embodiment of the invention, onion variety DULCIANA is crossed to produce onion seed derived of the variety designated DULCIANA. In any cross herein, either parent may be the male or female parent. In these processes, crossing will result in the production of seed. The seed production occurs regardless of whether the seed is collected or not.

In one embodiment of the invention, the first step in "crossing" comprises planting seeds of a first and a second parent onion plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of the first and the second parent onion plants into plants that bear flowers. A third step may comprise preventing self-pollination of the plants, such as by emasculating the male portions of flowers, (e.g., treating or manipulating the flowers to produce an emasculated parent onion plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step for a hybrid cross may comprise cross-pollination between the first and second parent onion plants. In certain embodiments, pollen may be transferred manually or by the use of insect vectors. Yet another step comprises harvesting the seeds from at least one of the parent onion plants. The harvested seed can be grown to produce an onion plant or hybrid onion plant.

The present invention also provides the onion seeds and plants produced by a process that comprises crossing a first parent onion plant with a second parent onion plant, wherein at least one of the first or second parent onion plants is a plant provided herein, such as from variety DULCIANA. In another embodiment of the invention, onion seed and plants produced by the process are first filial generation (F1) hybrid onion seed and plants produced by crossing a plant in accordance with the invention with another, distinct plant. The present invention further contemplates plant parts of such an F1 hybrid onion plant, and methods of use thereof. Therefore, certain exemplary embodiments of the invention provide an F1 hybrid onion plant and seed thereof.

In still yet another aspect, the present invention provides a method of producing a plant or a seed derived from variety DULCIANA, the method comprising the steps of: (a) preparing a progeny plant derived from said variety by crossing a plant of variety DULCIANA with a second plant; and (b) selfing the progeny plant or crossing it to the second plant or to a third plant to produce a seed of a progeny plant of a subsequent generation.

The method may additionally comprise: (c) growing a progeny plant of a further subsequent generation from said seed of a progeny plant of a subsequent generation and selfing the progeny plant of a subsequent generation or crossing it to the second, the third, or a further plant; and repeating the steps for 3 or more times, e.g., an additional 3-10 generations to produce a further plant derived from the aforementioned starting variety. The further plant derived from variety DULCIANA may be an inbred variety, and the aforementioned repeated crossing steps may be defined as comprising sufficient inbreeding to produce the inbred variety. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

One aspect of the invention refers to a method of producing an onion plant comprising crossing an onion plant of variety DULCIANA with a second onion plant one or more times. This method comprises in one embodiment selecting progeny from said crossing.

In another aspect of the invention, an onion plant of variety DULCIANA comprising an added heritable trait is provided, e.g., an Essentially Derived Variety of DULCIANA having one, two or three physiological and/or morphological characteristics which are different from those of DULCIANA and which otherwise has all the physiological and morphological characteristics of DULCIANA, wherein a representative sample of seed of variety DULCIANA has been deposited under NCIMB/ATTC Accession Number 42706. The heritable trait may comprise a genetic locus that is, for example, a dominant or recessive allele. In one embodiment of the invention, a plant of the invention is defined as comprising a single locus conversion. For example, one, two, three or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location. Thus, the invention comprises a method of producing a plant comprising an added desired trait, the method comprising introducing a transgene conferring the desired trait into a plant of onion variety DULCIANA.

For example, in certain embodiments, the invention provides methods of introducing a desired trait into a plant of the invention comprising: (a) crossing a plant of variety DULCIANA with a second onion plant that comprises a desired trait to produce F1 progeny, (b) selecting an F1 progeny that comprises the desired trait(s), e.g., one, two, three or more desired trait(s), (c) crossing the selected F1 progeny with a plant of variety DULCIANA to produce backcross progeny, and (d) selecting backcross progeny comprising the desired trait(s) and which otherwise has all the physiological and morphological characteristics of variety DULCIANA. Optionally, steps (c) and (d) can be repeated one or more times, e.g., three or more times such as three, four, five, six or seven times, in succession to produce selected fourth, fifth, sixth, seventh or eighth or higher backcross progeny that comprises the desired trait. The invention also provides onion plants produced by these methods.

Still yet another aspect of the invention refers to the genetic complement of an onion plant variety of the invention. The phrase "genetic complement" is used to refer to the aggregate of nucleotide sequences, the expression of which defines the phenotype of, in the present case, an onion plant of, or a cell or tissue of that plant. A genetic complement thus represents the genetic makeup of a cell, tissue or plant, and a hybrid genetic complement represents the genetic make-up of a hybrid cell, tissue or plant. The invention thus provides onion plant cells that have a genetic complement in accordance with the onion plant cells disclosed herein, and plants, seeds and plants containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that a plant of the invention or a first generation progeny thereof could be identified by any of the many well-known techniques such as, for example, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (see, e.g., EP 534 858), and Single Nucleotide Polymorphisms (SNPs).

In still yet another aspect, the present invention provides hybrid genetic complements, as represented by onion plant cells, tissues, plants, and seeds, formed by the combination of a haploid genetic complement of an onion plant of the invention with a haploid genetic complement of a second onion plant, preferably, another, distinct onion plant. In another aspect, the present invention provides an onion plant regenerated from a tissue culture that comprises a hybrid genetic complement of this invention.

In still yet another aspect, the invention provides a method of determining the genotype of a plant of the invention comprising detecting in the genome of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

In one embodiment of the invention, the invention provides a method for producing a seed of a variety derived from DULCIANA comprising the steps of (a) crossing an onion plant of variety DULCIANA with a second onion plant; and (b) allowing seed of a variety DULCIANA-derived onion plant to form. This method can further comprise steps of (c) crossing a plant grown from said variety DULCIANA-derived onion seed with itself or a second onion plant to yield additional variety DULCIANA-derived onion seed; (d) growing said additional variety DULCIANA-derived onion seed of step (c) to yield additional variety DULCIANA-derived onion plants; and optionally (e) repeating the crossing and growing steps of (c) and (d) to generate further variety DULCIANA-derived onion plants. For example, the second onion plant is of an inbred onion variety.

In certain embodiments, the present invention provides a method of producing onions comprising: (a) obtaining a plant of the invention, wherein the plant has been cultivated to maturity, and (b) collecting an onion bulb from said plant.

The invention also provides for a food or feed product comprising or consisting of a plant part described herein preferably an onion bulb or part thereof and/or an extract from a plant part described herein. The food or feed product may be fresh or processed, e.g., canned, steamed, boiled, fried, blanched and/or frozen, etc.

Any embodiment discussed herein with respect to one aspect of the invention applies to other aspects of the invention as well, unless specifically noted.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DEFINITIONS

In the description and tables herein, a number of terms are used. In order to provide a clear and consistent understanding of the specification and claims, the following definitions are provided:

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more" unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. The terms mentioned above also comprise the term "contain" which is limited to specific embodiments. Thus, one embodiment of the invention, when the terms "comprise," "have" and "include" are used to describe a plant, part thereof or a process, refers to an embodiment wherein the limiting term "contain" is used.

As used herein, "onion plant" or "onion" is a plant of genus *Allium* or a part thereof (e.g. a bulb). Onion includes all kinds of onions, such as short-day, intermediate-day and long-day onions according to bulb initiation in response to various lengths of daylight. Generally, a "short-day" length type onion plant (short-day, or SD, onion) responds to 11 to 12 hours of daylight for the initiation of bulb formation; an "intermediate-day" length type onion plant (intermediate-day, or ID, onion) needs 12 to 14 hours of daylight; and a "long-day" length type onion plant (long-day, or LD onion) requires about 14 or more contiguous hours of daylight for bulb formation to start. Onion includes, e.g., *Allium aggregatum* (e.g., chalottes and potato onion), *Allium cepa* and *Allium fistulosum*, and hybrids such as *Allium xproliferum*, *Allium xwakegi*, and the triploid onion *Allium xcornutum*. *Allium cepa* L. (common onion) is a cool season (tolerant of frost) biennial plant. By "biennial plant" it is meant that *Allium cepa* L. produces a bulb in the first season and seeds in the second. Onion plants may be grown at any temperature that allows for the growth and development of the plant.

"Cultivated onion" refers to plants of *Allium*, i.e. varieties, breeding lines or cultivars of the species *Allium cepa*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"USDA descriptors" are the plant variety descriptors described for onion in the "Objective description of Variety Onion *Allium cepa* L.", ST-470-16 (as published by U.S. Department of Agriculture, Agricultural Marketing Service, Science and Technology, Plant Variety Protection Office, Beltsville, Md. 20705 (available on the world wide web at www.ams.usda.gov/AMSv1.0/) and which can be downloaded from the world wide web at http://www.ams.usda-.gov/AMSv1.0/getfile?dDocName=STELDEV3003776.

"UPOV descriptors" are the plant variety descriptors described for onion in the "Guidelines for the Conduct of Tests for Distinctness, Uniformity and Stability, TG/46/7 (Geneva 2009), as published by UPOV (International Union for the Protection of New Varieties and Plants, available on the world wide web at upov.int) and which can be downloaded from the world wide web at http://www.upov.int/edocs/tgdocs/en/tg046.pdf and is herein incorporated by reference in its entirety.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested onion bulbs (tubers), leaves etc.), plant cells, plant protoplasts, plant cell and/or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, flowers, leaves, seeds, clonally propagated plants, roots, stems, root tips, grafts, parts of any of these and the like. Also any developmental stage is included, such as seedlings, cuttings prior or after rooting, mature plants or leaves.

By "bulb" or "onion bulb" is meant the (commercially) (harvested,) edible portion of the onion plant. An onion bulb comprises an apex and concentric, enlarged fleshy leaf bases, also called fleshy scale leaves (see, e.g., FIG. 1). Onion bulbs may be developing onion bulbs or mature onion bulbs.

"Harvested plant material" refers herein to plant parts (e.g. a bulb detached from parts of the plant (such as leaves) or the rest of the plant) which have been collected for further storage and/or further use.

"Maturity" refers to the development stage of an onion bulb when said onion bulb has fully developed (reached its final size). In particular embodiments "maturity" is defined as the mature state of bulb development and optimal time for harvest. Typically, maturity of a bulb is reached when the vegetative phase of an onion plant is over and leaves and neck of the onion plant dry out.

As used herein, a "mature onion bulb" refers to any onion bulb that is ready for harvest. Generally, when 25-50% of the onion leaf tops have fallen over, the onion is ready for harvest.

"Harvested seeds" refers to seeds harvested from a line or variety, e.g. produced after self-fertilization or cross-fertilization and collected.

A plant having "(essentially) all the physiological and morphological characteristics" means a plant having essentially all or all the physiological and morphological characteristics when grown under the same environmental conditions of the plant of DULCIANA from which it was derived, e.g. the progenitor plant, the parent, the recurrent parent, the plant used for tissue- or cell culture, etc. The skilled person will understand that a comparison between onion varieties should occur when said varieties are grown under the same environmental conditions. For example, the plant may have all characteristics mentioned in Table 1 when grown under the conditions of the field trial described in this application. In certain embodiments, the plant having "essentially all the physiological and morphological characteristics" are plants having all the physiological and morphological characteristics, except for certain characteristics, such as one, two or three, mentioned, e.g. the characteristic(s) derived from a converted or introduced gene or trait and/or except for the characteristics which differ in an EDV. So, the plant may have all characteristics mentioned in Table 1, except for one, two or three characteristics of Table 1, in which the plant may thus differ.

A plant having one or more or all "essential physiological and/or morphological characteristics" or one or more "distinguishing characteristics" (such as one, two, three, four or five) refers to a plant having (or retaining) one or more, or all, or retaining all except one, two or three of the distinguishing characteristics mentioned in Table 1 when grown under the same environmental conditions that distinguish DULCIANA from most similar variety SERENGETI such distinguishing characteristics being selected from (but not limited to): Color of bulb skin; bulb height; column length of sheath (height from soil line to base of lowest succulent leaf; plant height above soil line to highest point of any foliage; and maturity (see e.g. Table 1).

In a further embodiment, DULCIANA can be distinguished from SERENGETI, when grown under the same environmental conditions, by using the further distinguishing characteristics being selected from (but not limited to): length of leaf (before maturity yellowing begins); width of leaf; thickness of leaf (at mid-length of longest leaf); interior bulb color; and bulb weight (see e.g. Table 1).

The physiological and/or morphological characteristics mentioned above are commonly evaluated at significance levels of 1%, 5%, 8% or 10% significance level, when measured under the same environmental conditions. For example, a progeny plant of DULCIANA may have one or more (or all, or all except one, two or three) of the essential physiological and/or morphological characteristics of DULCIANA listed in Table 1, or one or more or all (or all except one, two or three) of the distinguishing characteristics of DULCIANA listed in Table 1 and above, as determined at the 1% or 5% significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

The terms "gene converted" or "conversion plant" in this context refer to onion plants which are often developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are often developed by plant breeding techniques comprising or consisting of backcrossing, wherein essentially all of the desired morphological and physiological characteristics of an onion variety are recovered in addition to the characteristics of the single locus having been transferred into the variety via, e.g., the backcrossing technique and/or by genetic transformation. Likewise, a double loci converted plant/a triple loci converted plant refers to plants having essentially all of the desired morphological and physiological characteristics of given variety, expect that at two or three loci, respectively, it contains the genetic material (e.g., an allele) from a different variety.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering. In one embodiment, an EDV is a gene converted plant.

"Plant line" is for example a breeding line which can be used to develop one or more varieties.

"Hybrid variety" or "F1 hybrid" refers to the seeds of the first generation progeny of the cross of two non-isogenic plants. For example, the female parent is pollinated with pollen of the male parent to produce hybrid (F1) seeds on the female parent.

"Progeny" as used herein refers to plants derived from a plant designated DULCIANA. Progeny may be derived by regeneration of cell culture or tissue culture or parts of a plant designated DULCIANA or selfing of a plant designated DULCIANA or by producing seeds of a plant designated DULCIANA. In further embodiments, progeny may also encompass plants derived from crossing of at least one plant designated DULCIANA with another onion plant of the same or another variety or (breeding) line, or with a wild onion plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of DULCIANA which are EDVs or which retain all (or all except 1, 2 or 3) physiological and/or morphological characteristics of DULCIANA listed in Table 1, or which retain all (or all except 1, 2, or 3) of the distinguishing characteristics of DULCIANA described elsewhere herein and in Table 1, are encompassed herein.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one onion line or variety to another.

"Crossing" refers to the mating of two parent plants.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) a bulb or part thereof, leaf, pollen, embryo, cotyledon, hypocotyl, cells, protoplasts, meristematic cell, root, root tip, pistil, anther, flower, shoot tip, shoot, stem, petiole, etc. When a whole plant is regenerated by vegetative propagation, it is also referred to as a vegetative propagation.

"Locus" (plural loci) refers to the specific location of a gene or DNA sequence on a chromosome. A locus may confer a specific trait.

"Linkage" refers to a phenomenon wherein alleles on the same chromosome tend to segregate together more often than expected by chance if their transmission was independent.

"Marker" refers to a readily detectable phenotype, preferably inherited in codominant fashion (both alleles at a locus in a diploid heterozygote are readily detectable), with no environmental variance component, i.e., a heritability of one (1).

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

"Tissue Culture" refers to a composition comprising isolated cells of the same or a different type or a collection of such cells organized into parts of a plant.

"Transgene" or "chimeric gene" refers to a genetic locus comprising a DNA sequence which has been introduced into the genome of an onion plant by transformation. A plant comprising a transgene stably integrated into its genome is referred to as "transgenic plant".

"Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Triploid" refers to a cell or organism having three sets of chromosomes.

"Tetraploid" refers to a cell or organism having four sets of chromosomes.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for oniondescribed herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p=0.05) from the mean.

DRAWINGS

The drawings described herein are for illustration purposes only and are not intended to limit the scope of the present teachings in any way.

FIG. 1 shows the differences in bulb shape and bulb color of typical onion bulbs of DULCIANA and SERENGETI.

DETAILED DESCRIPTION OF THE INVENTION

The invention provides methods and compositions relating to plants, plant parts, seeds and progenies of onion variety DULCIANA.

Variety DULCIANA exhibits a number of improved traits including: 1) a pinkish yellow color of bulb skin, e.g. RHS Orange-White Group 159A and Greyed-Yellow Group 160 C; 2) a (average) bulb height that is between about 6.0 and 8.4 cm, or preferably between about 6.6 and 7.8 cm, or between about 7.0 and 7.4 cm or even about 7.2 cm; 3) a (average) column length of sheath that is between about 40 and 52 mm, or preferably between 43 and 49 mm or even between about 45 and 47 mm, or even about 46 mm; 4) a (average) plant height above soil line to highest point of any foliage that is at least between about 58 cm and 68 cm, or preferably between about 60 cm and 64 cm or even between about 62 cm and 64 cm, or even about 63 cm; 5) early maturity (e.g. between 75-90 days).

In a further embodiment, further characteristics are at least one selected from: 6) (average) length of leaf (before maturity yellowing begins) that is at least between about 33 cm and about 58 cm, or preferably between about 43 cm and about 49 cm, or even between about 45 cm and 48 cm or even about 46 cm; 7) (average) width of leaf that is at least between about 15 mm and 25 mm, or preferably between about 18 mm and 23 mm, or even between about 20 mm and 22 mm, or even about 21 mm; 8) (average) thickness of leaf (at mid-length of longest leaf) that is at least between about 1.25 mm and 2.44 mm, or preferably between about 1.4 mm and 1.8 mm, or even between about 1.6 mm and 1.8 mm, or even about 1.7 mm; 9) an cream colored bulb interior, e.g. RHS White group 155A; 10) a (average) bulb weight of at least 200 grams, or preferably at least about 210 grams, 215 grams, 220 grams, 225 grams, 230 grams, 235 grams, 240 grams, or even about 241 grams.

Development of DULCIANA

The hybrid DULCIANA was made from male and female proprietary inbred lines developed by Nunhems. The female parent of DULCIANA and its maintainer was developed out of an internal breeding line. This inbred was developed over a period of 14 years/7 generations of inbreeding using single bulb selfing.

The male parent was developed from a [fertile×fertile] cross of two Nunhems inbred lines over a period of 8 generations of single bulb selfings.

The female and male parents were crossed to produce hybrid (F1) seeds of DULCIANA. The seeds of DULCIANA can be grown to produce hybrid plants and parts thereof (e.g. onion bulbs). The hybrid DULCIANA can be propagated by seeds or vegetative.

The hybrid variety is uniform and genetically stable. This has been established through evaluation of horticultural characteristics. Several hybrid seed production events resulted in no observable deviation in genetic stability. DULCIANA has been observed for more than three generations in different trials on different locations and during seed increase.

Coupled with the confirmation of genetic stability of the female and male parents the Applicant concluded that DULCIANA is uniform and stable.

Breeding of Onion Plants of the Invention

One aspect of the current invention concerns methods for crossing an onion variety provided herein with itself or a second plant and the seeds and plants produced by such methods. These methods can be used for propagation of a variety provided herein, or can be used to produce hybrid onion seeds and the plants grown therefrom. Such hybrid seeds can be produced by crossing the parent varieties of the variety.

The development of new varieties using one or more starting varieties is well known in the art. In accordance with the invention, novel varieties may be created by crossing a plant of the invention followed by multiple generations of breeding according to such well known methods. New varieties may be created by crossing with any second plant. In selecting such a second plant to cross for the purpose of developing novel varieties, it may be desired to choose those plants that either themselves exhibit one or more selected desirable characteristics or that exhibit the desired characteristic(s) when in hybrid combination. Once initial crosses have been made, inbreeding and selection take place to produce new varieties. For development of a uniform variety, often five or more generations of selfing and selection are involved.

Uniform varieties of new varieties may also be developed by way of double-haploids. This technique allows the creation of true breeding varieties without the need for multiple generations of selfing and selection. In this manner, true breeding varieties can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous variety.

Backcrossing can also be used to improve an inbred plant. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term variety DULCIANA is used in the context of the present invention, this also includes plants modified to include at least a first desired heritable trait such as one, two or three desired heritable trait(s).

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross are then mated back to the recurrent parent followed by selection in the resultant progeny (first backcross generation, or BC1) for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental onion plant which contributes the desired characteristic or characteristics is termed the non-recurrent parent because it can be used one time in the backcross protocol and therefore need not recur. The parental onion plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent variety was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of onion plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of onion are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

Onion varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

The varieties and varieties of the present invention are particularly well suited for the development of new varieties or varieties based on the elite nature of the genetic background of the variety. In selecting a second plant to cross with DULCIANA for the purpose of developing novel onion varieties, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), male fertility, improved harvest characteristics, enhanced nutritional quality, increased antioxidant content, improved processing characteristics, high yield, improved characteristics related to the bulb flavor, texture, size, shape, durability, shelf life, and yield, increased soluble solids content, uniform ripening, delayed or early ripening, adaptability for soil conditions, and adaptability for climate conditions. Of course, certain traits, such as disease and pest resistance, and high yield are of interest in any type of onion variety or variety.

Plants of the Invention Derived by Genetic Engineering

Many useful traits that can be introduced by backcrossing, as well as directly into a plant, are those that are introduced by genetic transformation techniques. Genetic transformation may therefore be used to insert a selected transgene into the onion variety of the invention or may, alternatively, be used for the preparation of varieties containing transgenes that can be subsequently transferred to the variety of interest by crossing. Methods for the transformation of plants, including tomato, are well known to those of skill in the art. Techniques which may be employed for the genetic transformation of onion include, but are not limited to, electroporation, microprojectile bombardment, *Agrobacterium*-mediated transformation, pollen-mediated transformation, and direct DNA uptake by protoplasts.

To effect transformation by electoporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproduction parts of onion plants for pollination. A pollen-mediated method for the transformation of onion is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the BIOLISTICS Particle Delivery System, which can be used to propel particles coated with DNA or cells through a screen, such as a stainless steel or Nytex screen, onto a surface covered with target onion-cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes.

The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (see, e.g., U.S. Pat. No. 5,563,055).

Transformation of plant protoplasts also can be achieved using methods based on calcium phosphate precipitation, polyethylene glycol treatment, electroporation, and combinations of these treatments which are well known in the art. Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for onion plant gene expression include, but are not limited to, the cauliflower mosaic virus (CaMV) P-35S promoter, which confers constitutive, high-level expression in most plant tissues, including monocots; a tandemly, partially duplicated version of the CaMV 35S promoter, the enhanced 35S promoter (P-e35S) the nopaline synthase promoter, the octopine synthase promoter; and the figwort mosaic virus (P-FMV) promoter (see, e.g., U.S. Pat. No. 5,378,619) and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding; or (5) chemicals such as methyl jasmonate, salicylic acid, or Safener. It may also be advantageous to employ organ-specific promoters.

Exemplary nucleic acids which may be introduced to the onionvarieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an onion plant according to the invention. Non-limiting examples of particular genes and corresponding phenotypes one may choose to introduce into an onion plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. No. 5,500,365 and U.S. Pat. No. 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. Thus, any gene which produces a protein or mRNA which expresses a phenotype or morphology change of interest is useful for the practice of the present invention.

Deposit Information

A total of 2500 seeds of the hybrid variety DULCIANA were deposited according to the Budapest Treaty by Nunhems B. V. on Dec. 15, 2016, at the NCIMB Ltd., Ferguson Building, Craibstone Estate, Bucksburn, Aberdeen AB21 9YA, United Kingdom (NCIMB). The deposit has been assigned Accession Number NCIMB 42706.

A deposit of DULCIANA and of the male and female parent line is also maintained at Nunhems B. V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

Characteristics of Dulciana

SERENGETI is considered to be the most similar variety to DULCIANA. SERENGETI is a commercial variety from Nunhems. In Table 1 a comparison between DULCIANA and SERENGETI is shown based on a trial in the USA. Trial location: Bakersfield, (Shafter Rd), Calif., USA (coordinates: 35°13'54" N, 118°54'12" W). Planting date: Dec. 16, 2011; evaluation date Mar. 15, 2012.

Two replications of 15 plants each, from which 20 plants or plant parts were randomly selected, were used to measure characteristics. In Table 1 the USDA descriptors of DULCIANA (this application) and reference SERENGETI (commercial variety) are listed.

In accordance with one aspect of the present invention, there is provided a plant having the physiological and morphological characteristics of onion variety DULCIANA. A description of the physiological and morphological characteristics of onion variety DULCIANA is presented in Table 1.

TABLE 1

| Comparison between values* of DULCIANA and SERENGETI | | |
|---|---|---|
| Descriptor | Application Variety DULCIANA | Comparison Variety SERENGETI |
| 1. TYPE: | | |
| 1 = Bulb 2 = Bunching | 1 | 1 |
| 1 = short day; 2 = long day | 1 | 1 |
| Adaptation range | 35N to 35S | 35N to 35S |
| Degree mean latitude | | |
| Maturity (days) | 1 | 2 |
| 1 = early (75-90); | | |
| 2 = medium (100-120); | | |
| 3 = late (>130) | | |
| 2. PLANT: | | |
| Height above soil line to highest point of any foliage | 63 cm | 73 cm |
| Shorter than comparison variety | 10 cm | — |
| 1 = erected (Spartam Gem); | 1 | 2 |
| 2 = intermediate; | | |
| 3 = floppy (Epoch) | | |
| 3. LEAF: | | |
| Length (before maturity yellowing begins) | 46 cm | 60 cm |
| Width | 21 mm | 27 mm |
| Thickness (at mid-length of longest leaf) | 1.7 mm | 2.2 mm |
| Color: | 2 | 2 |
| 1 = light green (Early Grano); | | |
| 2 = medium green (Yellow Bermuda); | | |
| 3 = blue green (Australian Brown U.C. No. 1) | | |
| Color Chart Name | RHS Yellow Green Group | RHS Yellow Green Group |
| Color Chart Code | 147B | 147B |
| Bloom: | 2 | 2 |
| 1 = none-glossy; | | |
| 2 = light (Early Grano); | | |
| 3 = medium (Crystal Wax); | | |
| 4 = heavy (California Early Red) | | |
| 4. SHEATH: | | |
| Column length (height from soil line to base of lowest succulent leaf) | 46 mm | 88 mm |
| 5. INFLORESCENCE: | | |
| Pollen viability 1 = sterile; 2 = fertile | 2 | 2 |
| 6. BULB: | | |
| Size (harvested) | 3 | 3 |
| 1 = small (Red Creol); | | |
| 2 = medium (Australian Brown U.C. No. 1); | | |
| 3 = large (Early Grano) | | |
| Shape | ¼ (between a globe and a top shape) | ¼ (between a globe and a top shape) |
| 1 = Globe (White Sweet Spanish) | | |
| 2 = Deep Globe (Abundance) | | |
| 3 = Flt. Globe (Australian Brn. U.C. No. 1) | | |
| 4 = Top Shape (Texas Grano 502) | | |
| 5 = Deep Flat (Granex) | | |
| 6 = Thick Flat (Ebenezer) | | |
| 7 = Flat (Crystal Wax) | | |
| 8 = Torpedo-Long Oval (Italian Red) | | |
| Height | 7.2 cm | 7.7 cm |
| Diameter | 8.3 cm | 8.4 cm |

TABLE 1-continued

Comparison between values* of DULCIANA and SERENGETI

| Descriptor | Application Variety DULCIANA | Comparison Variety SERENGETI |
|---|---|---|
| Shape Index | 0.87 | 0.92 |
| 1 = invaginate; 2 = evaginate | 2 | 2 |
| Color (skin): | 04 | 05 |
| 01 = Brown (Australian Brn. U.C. No. 1) | (RHS | (RHS |
| 02 = Purplish Red (Italian Red) | Orange-White | Greyed-Yellow |
| 03 = Buff Red (Red Creole) | 159C + | 162C + |
| 04 = Pinkish Yellow (Ebenezer) | Greyed-Yellow | Greyed-Orange |
| 05 = Brownish Yellow (Mt. Danvers) | 160C) | 163A) |
| 06 = Deep Yellow (Brigham Yellow Globe) | | |
| 07 = Medium Yellow (Early Yellow Globe) | | |
| 08 = Pale Yellow (Yellow Bermuda) | | |
| 09 = White (White Sweet Spanish) | | |
| 10 = Other (Specify) | | |
| Color (interior) | 5 | 5 |
| 1 = Pink; 2 = Red; 3 = Purplish Red; 4 = White; | (RHS | (RHS |
| 5 = Cream; 6 = Light Green-Yellow; 7 = Dark Green-Yellow | White 155A) | White 155B) |
| Weight** | 241 grams | 287 grams |
| Scales: | 1 | 1 |
| 1 = Few (Crystal Wax) | | |
| 2 = Medium (Australian Brown U.C. No. 1) | | |
| 3 = Many (Sweet Spanish) | | |
| Scales: | 3 | 3 |
| 1 = Thick (Australian Brown U.C. No. 1) | | |
| 2 = Medium (Red Creole) | | |
| 3 = Thin (Crystal Wax) | | |
| Scale retention: | 3 | 3 |
| 1 = Very Good (Australian Brn. U.S. No. 1) | | |
| 2 = Good (Ebenezer) | | |
| 3 = Fair (Red Wethersfield) | | |
| 4 = Poor (Crystal Wax) | | |
| Pugence: | 1 | 1 |
| 1 = Mild (Early Grano) | | |
| 2 = Medium (Crystal Wax) | | |
| 3 = Strong (White Creole) | | |
| Storage: | 3 | 3 |
| 1 = Good (Ebenezer) | | |
| 2 = Fair (Yellow Globe Danvers) | | |
| 3 = Poor (Crystal Wax) | | |
| 7. DISEASE RESISTANCE | | |
| 0 = not tested; 1 = susceptible 2 = resistant | | |
| Black Mold | 0 | 0 |
| Neck Mold | 0 | 0 |
| Puple Blotch | 0 | 0 |
| Smut | 0 | 0 |
| Mildew | 0 | 0 |
| Pink root | 2 | 2 |
| Smudge | 0 | 0 |
| Yellow dwarf | 0 | 0 |
| 8. INSECT RESISTANT | | |
| 0 = not tested; 1 = susceptible 2 = resistant | | |
| Thrip | 0 | 0 |
| Other (specify) | | |
| Indicate a variety that most closely resembles that submitted: | SERENGETI | DULCIANA |
| Leaf height (mm) | | |
| Leaf color | | |
| Leaf bloom/wax | | |
| Flower stalk | | |
| Maturity at same location (D days) | | |
| Flower ball | | |
| Bulb color | | |
| Bulb size | | |
| Bulb shape | | |

*These are typical values. Values may vary due to environment. Other values that are substantially equivalent are also within the scope of the invention.
**No USDA descriptor As described above, variety DULCIANA exhibits desirable agronomic traits, including: 1) a pinkish yellow bulb skin color, e.g. RHS Orange-White Group 159A and Greyed-Yellow Group 160C, whereas SERENGETI has a brownish yellow bulb skin color, e.g. RHS Greyed-Yellow Group 162C and Greyed-Orange Group 163A; 2) a (average) bulb height that is at least about 4%, or preferably about 4.5%, 5%, 5.5%, 6%, or even about 6.5% smaller than the bulb height of SERENGETI; 3) a (average) column height of sheath (height form soil line to base of lowest succulent leaf) that is at least about 35%, or preferably about 40%, 41%, 42%, 43%, 44%, 45%, 46%, 47%, or even about 47.7% smaller than the column height of sheath of SERENGETI; 4) a (average) plant height above soil line to highest point of any foliage that is at least about 7.5%, or preferably about 8%, 9%, 10%, 11%, 12%, 13%, or even about 13.7% smaller than the plant height above soil line to highest point of any foliage of SERENGETI; 5) early maturity (75-90 days), whereas SERENGETI has medium maturity (100-120 days).

In a further embodiment, variety DULCIANA exhibits other desirable agronomic traits, including: 6) a (average) length of leaf (before maturity yellowing begins that is at least about 15%, or preferably about 16%, 17%, 18%, 19%, 20%, 21%, 22%, 23%, or even about 23.3% smaller than the leaf length of SERENGETI; 7) a (average) leaf width that is at least about 15%, or preferably about 16%, 17%, 18%, 19%, 20%, 21%, 22%, or even about 22.2% smaller than the leaf width of SERENGETI; 8) a (average) thickness of leaf (at mid-length of longest leaf) that is at least about 15%, or preferably about 16%, 17%, 18%, 19%, 20%, 21%, 22%, or even about 22.7% smaller than the leaf thickness of SERENGETI; 9) a cream colored bulb interior, e.g. RHS White Group 155A, whereas SERENGETI has a lighter cream color, e.g. RHS White Group 155B; 10) a (average) bulb weight that is at least about 10%, or preferably about 11%, 12%, 13%, 14%, 15%, or even about 16% smaller than the bulb weight of SERENGETI.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
U.S. Pat. No. 6,806,399
WO 99/31248
EP 0 534 858
Choi et al., Plant Cell Rep., 13: 344-348, 1994.
Ellul et al., Theor. Appl. Genet., 107:462-469, 2003.

What is claimed is:

1. An onion plant of variety DULCIANA, a representative sample of seed of said variety having been deposited under ATCC Accession Number 42706.

2. A seed of variety DULCIANA, a representative sample of seed of said variety having been deposited under ATCC Accession Number 42706.

3. A plant part of the plant of claim 1, further defined as a leaf, pollen, an ovule, a bulb, or a cell.

4. The plant part of claim 3, further defined as a bulb.

5. An onion plant, or a part thereof, which has all the characteristics listed in Table 1 for the onion plant of claim 1, when grown under the same conditions.

6. A tissue culture of regenerable cells of the plant of claim 1.

7. The tissue culture according to claim 6, comprising cells or protoplasts from a plant part selected from the group consisting of embryos, meristems, cotyledons, pollen, leaves, anthers, roots, root tips, pistil, flower, seed and bulbs.

8. An onion plant regenerated from the tissue culture of claim 6, the plant having all the physiological and morphological characteristics of a plant of claim 1 as provided in Table 1.

9. A method of vegetatively propagating the plant of claim 1 comprising the steps of:
   (a) collecting tissue capable of being propagated from a plant according to claim 1;
   (b) cultivating said tissue to obtain proliferated shoots; and
   (c) rooting said proliferated shoots to obtain rooted plantlets.

10. The method of claim 9, further comprising growing plants from said rooted plantlets.

11. A method of introducing a desired trait into an onion variety comprising:
   (a) crossing the plant of claim 1 with a second onion plant that comprises a desired trait to produce F1 progeny;
   (b) selecting an F1 progeny that comprises the desired trait;
   (c) crossing the selected F1 progeny with a plant of variety DULCIANA to produce backcross progeny;
   (d) selecting backcross progeny comprising the desired trait and all or essentially all the physiological and morphological characteristic of onion variety DULCIANA; and optionally
   (e) repeating steps (c) and (d) one or more times in succession to produce selected fourth or higher backcross progeny that comprise the desired trait.

12. A method of determining the genotype of the plant of claim 1 comprising obtaining a sample of nucleic acids from said plant and detecting in said nucleic acids a plurality of polymorphisms.

13. The method of claim 12, further comprising the step of storing the results of detecting the plurality of polymorphisms on a computer readable medium.

14. A method for producing a seed of a variety derived from the plant of claim 1, comprising the steps of:
   (a) crossing an onion plant of variety DULCIANA with a second onion plant; and
   (b) allowing seed of a variety DULCIANA-derived onion plant to form.

15. The method of claim 14 further comprising the steps of:
   (c) crossing a plant grown from said variety DULCIANA-derived onion seed with itself or a second onion plant to yield additional variety DULCIANA-derived onion seed;
   (d) growing said additional variety DULCIANA-derived onion seed of step (c) to yield additional variety DULCIANA-derived onion plants; and optionally
   (e) repeating the crossing and growing steps of (c) and (d) to generate further variety DULCIANA-derived onion plants.

16. The method of claim 14, wherein the second onion plant is of an inbred onion variety.

17. A method of producing an onion bulb comprising:
   (a) obtaining a plant according to claim 1, wherein the plant has been cultivated to maturity; and
   (b) collecting a bulb from said plant.

18. A food or feed product comprising a plant part of claim 3, wherein the plant part is an onion bulb or part thereof of the plant of claim 1.

19. A container comprising the plant part of claim 4.

* * * * *